US00PP19971P2

(12) United States Plant Patent
Ault

(10) Patent No.: US PP19,971 P2
(45) Date of Patent: Apr. 28, 2009

(54) ***BAPTISIA* PLANT NAMED 'STARLITE'**

(50) Latin Name: *Baptisia×bicolor*
Varietal Denomination: Starlite

(75) Inventor: James R. Ault, Libertyville, IL (US)

(73) Assignee: Chicagoland Grows, Glencoe, IL (US)

( * ) Notice: Subject to any disclaimer, the term of this patent is extended or adjusted under 35 U.S.C. 154(b) by 11 days.

(21) Appl. No.: 11/982,691

(22) Filed: Nov. 2, 2007

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

Anonymous. Walters Gardens, *Baptisia* Starlite Prarie Blues. available at: http://www.waltersgardens.com/index-.cfm?fuseaction=plants.plantDetail&plant_id=1747&printLayout=1.*

* cited by examiner

*Primary Examiner*—Wendy C. Haas
(74) *Attorney, Agent, or Firm*—Penny J. Aguirre

(57) ABSTRACT

A new cultivar of interspecific *Baptisia,* 'Starlite', characterized by its early blooming bicolor flowers that are violet-purple with a yellow keel held, its densely flowered inflorescences, its initially upright then cascading plant habit, its vigorous growth habit, and its hardiness in U.S.D.A. Zones 4 to 8.

2 Drawing Sheets

Botanical classification: *Baptisia×bicolor.*
Cultivar designation 'Starlite'.

BACKGROUND OF THE INVENTION

The present invention relates to a new and distinct cultivar of hybrid *Baptisia* plant, botanically known as *Baptisia× bicolor* 'Starlite' and will be referred to hereafter by its cultivar name, 'Starlite'. The new cultivar represents a new false indigo, an herbaceous perennial grown for landscape use.

The new invention arose from an ongoing controlled breeding program in Glencoe, Ill. The objectives of the breeding program were to develop interspecific hybrids of the genus *Baptisia* with unique and superior garden attributes. It was anticipated that interspecific *Baptisia* hybrids would yield plants with novel flower colors, varied plant habits and bloom seasons, improved foliage, greater low temperature hardiness, and better adaptability to garden soil conditions (soil type, moisture availability, pH, etc.).

'Starlite' was derived from an F1 cross made in 1998 in Libertyville, Ill. under controlled conditions (that excluded natural pollinators) between an unnamed plant of *Baptisia australis* as the female parent and an unnamed plant of *Baptisia bracteata* (syn. *Baptisia leucophaea*) as the male parent. The resulting seedlings were planted for evaluation in Glencoe, Ill. in spring of 1999. 'Starlite' was selected in 2001 as a single unique plant amongst the resulting seedlings.

Asexual reproduction of the new cultivar was first accomplished by stem cuttings in 2002 in Glencoe, Ill. by the inventor. The characteristics of this cultivar have been determined to be stable and are reproduced true to type in successive generations.

SUMMARY OF THE INVENTION

The following traits have been repeatedly observed and represent the characteristics of the new cultivar as observed for six years in Glencoe, Ill. These attributes in combination distinguish 'Starlite' from other cultivars of *Baptisia* known to the inventor.

1. 'Starlite' exhibits bi-color flowers; pale yellow keels with the other petals lavender to periwinkle blue.
2. 'Starlite' blooms earlier than most *Baptisia* species and cultivars; blooming in early to late May in Northern, Ill.
3. 'Starlite' is more floriferous and has better flower coverage than either of the parent species.
4. 'Starlite' exhibits a more vigorous growth habit than most *Baptisia.*
5. 'Starlite' has a plant habit that is initially vase-shaped becoming broad-rounded with age and has the appearance of a low dense shrub.
6. 'Starlite' is hardy in U.S.D.A. Zones 4 to 8.

In comparison to the female parent, *Baptisia australis,* 'Starlite' has lavender to blue flowers with a yellow keel whereas *Baptisia australis* has solid blue-violet flowers. 'Starlite' also differs in having flowers more densely borne on the inflorescences, in having a less upright plant habit, and is shorter in height. In comparison to the male parent, *Baptisia bracteata,* 'Starlite' has lavender to blue flowers with a yellow keel, glabrous stems and foliage, racemes that are initially upright then becoming arching, and flowers that are orientated in all directions on the stems whereas *Baptisia bracteata* has pale yellow flowers, pubescent stems and foliage, and flowers that are orientated in only one direction on the stems. The closest comparison plant is *Baptisia* 'Twilite' (U.S. Plant Pat. No. 19,011); it is also an interspecific hybrid from the same breeding program with bi-color flowers, however it is a *Baptisia ×variicolor,* has a more upright plant habit, blooms one to two weeks later, and has flowers that are violet purple with a yellow keel.

BRIEF DESCRIPTION OF THE DRAWING

The accompanying colored photographs illustrate the overall appearance and distinct characteristics of the new

*Baptisia.* The photographs were taken of plants and plant parts of a plant six years in age as grown outdoors in Glencoe, Ill.

Figure 1:
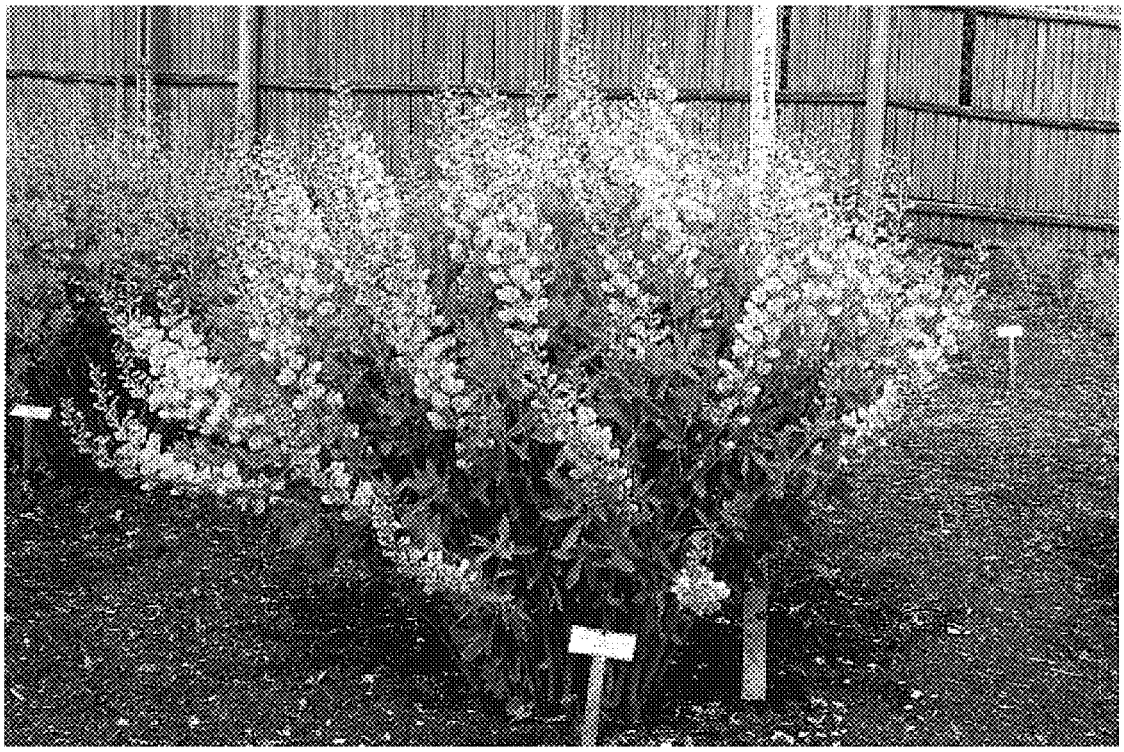

The photograph in FIG. 1 is a view of a plant of 'Starlite' in bloom and illustrates the dense, uniform habit and the abundance of flowers stems.

Figure 2:
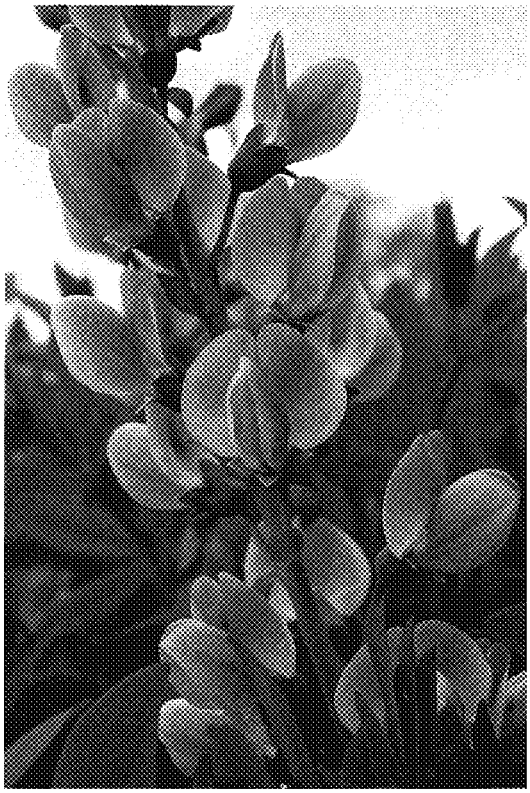

The photograph in FIG. 2 is of a close-up view of the flowers of 'Starlite'.

Figure 3:
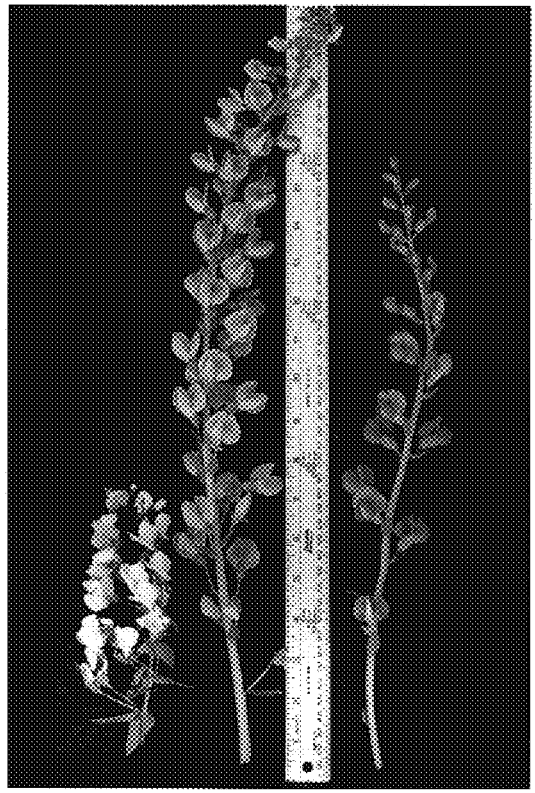

The photograph in FIG. 3 compares flower stems of 'Starlite' with the parent species; 'Starlite' is in the center, *Baptisia bracteata* is on the left, and *Baptisia australis* is on the right.

The colors in the photographs are as close as possible with the photographic and printing technology utilized. The color values cited in the detailed botanical description accurately describe the colors of the new *Baptisia.*

DETAILED BOTANICAL DESCRIPTION OF THE PLANT

The following is a detailed description of 6 year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—About 3 weeks in early to late May in Northern Illinois.

*Plant habit.*—Perennial, initially upright and becoming broadly rounded with a dense shrub-like form when mature.

*Height and spread.*—Reaches a height of about 90 cm and a spread of about 1.5 m in 4 years, and about 100 cm in height and 1.5 m in width in 8 years (excluding inflorescences).

*Hardiness.*—U.S.D.A. Zones 4 to 8.

*Culture.*—Prefers well-drained to medium moist soils in full sun, very tolerant to lean soils and drought, long lived.

*Diseases and pests.*—No susceptibility to any diseases or pests has been observed.

*Root description.*—Deep rooted, fibrous.

Growth and propagation:

*Propagation.*—Stem cuttings; 4 to 6 inch terminal cuttings taken from late May to early July, dipped in 1,250 ppm K-IBA and rooted in propagation media under mist or fog in a greenhouse root in two to four weeks.

*Growth rate.*—Medium to vigorous relative to other *Bapisia* species and cultivars.

Stem description:

*Branch habit.*—Densely branched; each stem typically produces 3 to 5 primary branches, the latter in turn bearing 3 to 10 secondary branches.

*Stem size.*—Reaches up to 100 cm in length (8 years, including peduncle), average of 6 to 7 mm in stem thickness.

*Stem shape.*—Oval.

*Stem color.*—144A to 144B.

*Stem surface.*—Glabrous, finely ribbed.

Foliage description:

*Leaf shape.*—Fan-shaped in overall outline.

*Leaf division.*—3-palmate.

*Leaf internode.*—Average of 5 cm.

*Leaf size.*—Up to 7.5 cm in length and 15 cm in width when mature.

*Leaflet shape.*—Oblanceolate.

*Leaflet base.*—Cuneate.

*Leaflet apex.*—Acute to rounded.

*Leaflet venation.*—Pinnate pattern, not conspicuous, color matches leaflet color on the upper and lower surface with the mid rib of lower surface 144A.

*Leaflet margins.*—Entire.

*Leaf attachment.*—Petiolate (short).

*Leaf arrangement.*—Alternate.

*Leaflet surface.*—Glabrous on upper and lower surface.

*Leaflet color.*—Newly expanded; upper surface between 144A and 144B, lower surface 144B, mature; upper; and lower surface 137A.

*Leaflet size.*—Up to about 7.5 cm in length, up to about 2.5 cm in width.

*Petioles.*—Average of 2.5 mm in length and 2 mm in width, clasping to stem at mature nodes, 144C in color, surface is glabrous.

*Stipules.*—Lanceolate in shape, base is truncate to stem, apex is narrowly acute to acuminate, average of 2.2 cm in length and 8 mm in width, 137A in color on upper and lower surface.

Flower description:

*Inflorescence type.*—Terminal and auxiliary racemes of bi-color pea-like flowers, opening from the base to the apex.

*Inflorescence size.*—Average length of 40 cm (measured from lowermost flower to inflorescence tip) and width of 4.5 cm; maximum length of 60 cm.

*Lastingness of inflorescence.*—3 to 4 weeks.

*Flower size.*—About 2.6 cm in depth and about 2 cm in diameter.

*Flower fragrance.*—Non detected.

*Flower number.*—About 50 per terminal racemes.

*Peduncle.*—Oval in shape, up to 60 cm in length and ranges from 5 cm in width at the base of the inflorescence to 2 mm in width at the apex, 144A to 144B in color, surface is glabrous and satiny with very scarce fine hairs, flower internode length ranges from 3 mm to 1.5 cm with an average of 7 mm.

*Petiole.*—About 7 mm in length, about 1.3 mm in width, oval in shape, 144B in color, satiny surface.

*Flower buds.*—Reniformed, about 2.4 cm in length and 8 mm in width, blend of 86C to 86D and N87C to N87D, calyx portion same as open flowers.

*Flower type.*—Papilionaceous.

*Flower orientation.*—Held at about a 45° angle in all directions.

*Calyx.*—Campanulate, about 9 mm in length and 7 mm in diameter, surface has satin sheen, 144C to 144D in color, persistent.

*Sepals.*—5, fused with the exception of apex of each, free portion is triangular in shape 3.5 mm in width and 3 mm in depth with an acute apex, 144C to 144D in color.

*Corolla features.*—Papilionaceous (4 segments) with a keel, an inner lip and 2 lateral wings, the inner lip; comprised of two lobes that are folded around stamens and pistil, lobes are reniform in shape, about 1.8 cm in length and 8 mm in width, color of inner and outer surface is a blend of 1C and 2D, rounded apex, base is notched inward, lateral wings; loosely surround inner lip, oblong in shape, about 2.2 cm in length and 1 cm in width, color of upper and lower surface is 155D heavily suffused with 91A and 91B, rounded apex, base is oblique with an attenuated section keel; reflexed, orbicular in shape, cordate apex, truncate base, 2.2 in length and 1.7 width, color of upper and lower surface is 91A and 91B with 155D towards bases surrounding a middle region of 144D and, all segments; glabrous in texture, entire margin.

*Receptacle.*—Disk-shaped, gelatinous, 144B in color, about 4 mm in diameter and 1.2 mm in depth.

Reproductive organs:

*Gynoecium.*—1 Pistil, about 1.8 cm in length, 1 mm in width; style is 144D in color; stigma minute, too small to color read; Ovary is superior with a stipe, 144B in color, 8 mm in length and 1 mm in width; stipe is 144D in color, 4 mm in length and <1 mm in width.

*Androcoecium.*—10 stamens, not united, 1.9 cm in length and 1 mm in width; filament is 1.8 cm in length, 1 mm in width and 144D in color; anther is dorsifixed, 1 mm in length, <1 mm in width and 163A in color, pollen is abundant and 144D in color.

*Fruit.*—An inflated pod, technically a legume, globose-oblongoid in shape, 2.5 to 5.5 cm in length by about 1 to 1.5 cm in width; each with a short beak approx. 7 mm in length, emerges green, 144B to 144C and matures in August to charcoal black 202A flushed with 200C, walls about 1.5 mm in thickness and woody at maturity. Seed 2 to 3 per fruit (open-pollinated), 200A in color, oval with the hilum side more or less straight, seed compressed to flattish, about 4 mm long×3 mm wide×1.3 mm in thickness.

I is claimed:

1. A new and distinct cultivar of *Baptisia* plant named 'Starlite' as herein illustrated and described.

* * * * *